(12) United States Patent
Ohtake

(10) Patent No.: US 7,806,824 B2
(45) Date of Patent: Oct. 5, 2010

(54) ULTRASOUND DIAGNOSIS APPARATUS

(75) Inventor: Akifumi Ohtake, Mitaka (JP)

(73) Assignee: Aloka Co., Ltd., Tokyo (JP)

(*) Notice: Subject to any disclaimer, the term of this patent is extended or adjusted under 35 U.S.C. 154(b) by 1066 days.

(21) Appl. No.: 10/964,422

(22) Filed: Oct. 13, 2004

(65) Prior Publication Data

US 2005/0119569 A1 Jun. 2, 2005

(30) Foreign Application Priority Data

Oct. 22, 2003 (JP) ............ 2003-361932

(51) Int. Cl.
*A61B 8/00* (2006.01)
(52) U.S. Cl. ............ 600/443; 600/442; 600/437; 600/407
(58) Field of Classification Search ......... 600/424–429, 600/437–472; 128/898, 916
See application file for complete search history.

(56) References Cited

U.S. PATENT DOCUMENTS

| | | | | |
|---|---|---|---|---|
| 4,390,025 A * | 6/1983 | Takemura et al. | ............ | 600/440 |
| 5,211,167 A | 5/1993 | Amenomori | | |
| 5,443,489 A * | 8/1995 | Ben-Haim | ............ | 607/115 |
| 5,558,091 A | 9/1996 | Acker et al. | | |
| 5,713,357 A * | 2/1998 | Meulenbrugge et al. | .... | 600/411 |
| 6,047,218 A * | 4/2000 | Whayne et al. | ............ | 607/122 |
| 6,370,411 B1 | 4/2002 | Osadchy et al. | ............ | 600/372 |
| 6,500,118 B1 | 12/2002 | Hashimoto | | |
| 6,522,913 B2 * | 2/2003 | Panescu et al. | ............ | 600/478 |
| 6,537,221 B2 | 3/2003 | Criton et al. | | |
| 6,547,735 B1 * | 4/2003 | Henderson | ............ | 600/443 |
| 6,572,547 B2 * | 6/2003 | Miller et al. | ............ | 600/437 |
| 6,592,520 B1 * | 7/2003 | Peszynski et al. | ............ | 600/437 |
| 6,607,488 B1 | 8/2003 | Jackson et al. | | |
| 6,673,018 B2 | 1/2004 | Friedman | | |
| 7,074,185 B2 * | 7/2006 | Takeuchi | ............ | 600/437 |
| 2003/0093067 A1 * | 5/2003 | Panescu | ............ | 606/32 |
| 2004/0019270 A1 | 1/2004 | Takeuchi | | |
| 2004/0122310 A1 | 6/2004 | Lim | | |
| 2005/0203417 A1 | 9/2005 | Okuno | | |
| 2007/0010743 A1 | 1/2007 | Arai | | |

FOREIGN PATENT DOCUMENTS

| | | |
|---|---|---|
| JP | 62-68442 | 3/1987 |
| JP | 5-300907 | 11/1993 |
| JP | H8-616 | 1/1996 |
| JP | 10-137242 | 5/1998 |

(Continued)

*Primary Examiner*—Brian Casler
*Assistant Examiner*—Nasir Shahrestani
(74) *Attorney, Agent, or Firm*—H. Henry Koda; William L. Androlia

(57) ABSTRACT

In a medical ultrasound diagnosis apparatus, a reference image and a guidance display are provided as probe operation support information. The reference image contains a recorded probe mark generated based on coordinate data recorded during a past diagnosis and a current probe mark generated based on current coordinate data. A user adjusts a position and an orientation of a probe so that these marks match. The guidance display has a plurality of indicators provided corresponding to a plurality of coordinate components. Each indicator displays proximity and match for each coordinate component. With the probe operation support information, it is possible to quickly and easily match a current diagnosis part to a past diagnosis part.

10 Claims, 6 Drawing Sheets

FOREIGN PATENT DOCUMENTS

| | | |
|---|---|---|
| JP | 11-47133 | 2/1999 |
| JP | 11-123187 | 5/1999 |
| JP | 2000-107185 | 4/2000 |
| JP | 2000-201926 | 7/2000 |
| JP | 2001-17433 | 1/2001 |
| JP | 2003-126091 | 2/2003 |
| WO | WO 00-64367 A | 11/2000 |
| WO | WO 02-09611 A2 | 2/2002 |
| WO | WO 02-24049 A2 | 3/2002 |

* cited by examiner

ULTRASOUND DIAGNOSIS APPARATUS

BACKGROUND OF THE INVENTION

1. Field of the Invention

The present invention relates to an ultrasound diagnosis apparatus, and in particular to a technique for supporting a probe operation (position and/or orientation adjustment) by a user.

2. Description of the Related Art

An ultrasound diagnosis apparatus has a function to display, on a screen of a display device, "a body mark (body symbol)" and a "probe mark (probe symbol)" as reference images along with an ultrasound image (image of living tissue, or living body image). The body mark is typically a simple, two-dimensional figure schematically representing a partial shape within a living body. A user may operate the device to select a specific body mark corresponding to a body part to be diagnosed using ultrasound from among a plurality of body marks which are prepared in advance. The body mark is displayed near the living body image. In order to identify a position and direction of the probe during ultrasound diagnosis, a probe mark is displayed overlapping the body mark. The probe mark is typically a figure of a simple line or simple box. The user can freely set the position and direction of the probe mark on the body mark. These marks are important information for identifying the part for which the living body image is obtained, on the display screen or in an examination report.

In order to evaluate progress of a disease and status of healing, comparative observation of a past ultrasound image and a current ultrasound image for a same patient is performed. During this process, it is necessary to match, to the highest possible degree, the current position and the current orientation of the probe with the past position and the past orientation of the probe corresponding to the time when the past ultrasound image is obtained, because it is necessary to perform the current ultrasound diagnosis with respect to a same part as the part to which the past ultrasound diagnosis is applied. For this purpose, a two-screen display function provided in the ultrasound diagnosis apparatus is utilized. For example, a past ultrasound image is displayed on the left half of the display screen and a current ultrasound image is simultaneously displayed on the right half of the display screen. The user operates the probe while comparatively observing both images so that the content of the current ultrasound image becomes closer to the past ultrasound image. In this manner, it is possible for the user to find an appropriate position and an appropriate orientation of the probe in the current ultrasound examination through a trial and error process.

Japanese Patent Laid-Open Publication No. 2000-201926 discloses an apparatus in which a three-dimensional body mark and a three-dimensional probe mark are displayed. In this apparatus, when a user changes a position of a probe mark, display content of a body mark is automatically changed so that the position of the probe mark is at a center position of the body mark. Japanese Patent Laid-Open Publication No. 2001-017433 also discloses an apparatus in which a three-dimensional body mark and a three-dimensional probe mark are displayed. In this apparatus, a body mark and a probe mark seen from a viewing direction designated by the user using an input unit are generated. A probe mark is displayed on an appropriate position on a body mark based on an actual positional relationship between a living body and the probe. In this case, the actual positional relationship is measured using a magnetic sensor (refer to paragraph 0025 of Japanese Patent Laid-Open Publication No. 2001-017433).

None of the references, however, discloses a technique for supporting a probe operation to match the current diagnosis part to the past diagnosis part.

Generally, users, such as a physician, an ultrasound examination technician, or the like, require significant experience to operate the probe to quickly and precisely match the current diagnosis part to the past diagnosis part. In addition, even for an expert user, the probe operations are complex. Further, even for an expert user, the optimum probe position and the optimum probe orientation may not be easily found. In particular, when the user during the past ultrasound diagnosis differs from the user in the current ultrasound diagnosis, these problems become more significant. When the diagnosis part of the past and the diagnosis part of the current differ, there is a problem in that an accurate diagnosis is not possible. This problem occurs because of a deviation of the probe position, deviation of the probe orientation, or both. Therefore, in order to prevent or reduce these problems, a support for the probe operations is desired.

SUMMARY OF THE INVENTION

The present invention advantageously provides an ultrasound diagnosis apparatus in which probe operation is supported to reduce load of the user.

The present invention advantageously provides an ultrasound diagnosis apparatus in which the current diagnosis part can be quickly and easily matched or approximated to the past diagnosis part.

The present invention advantageously provides an ultrasound diagnosis apparatus in which a disease can be properly evaluated or diagnosed based on a comparative observation between a past ultrasound image and a current ultrasound image.

(1) According to one aspect of the present invention, there is provided an ultrasound diagnosis apparatus comprising a probe which transmits and receives ultrasound and outputs received data, a coordinate measuring unit which measures at least one of a spatial position and orientation of the probe and outputs coordinate data representing a result of measurement, a coordinate storage unit which records recorded coordinate data, an information generator unit which generates probe operation support information based on the recorded coordinate data recorded in the coordinate storage unit and current coordinate data which is coordinate data currently output from the coordinate measuring unit, and an information provision unit which provides the probe operation support information to a user.

With the above-described structure, recorded coordinate data is stored in advance through an instruction by a user or in an automatic manner. Probe operation support information is generated based on the recorded coordinate data and the current coordinate data which is currently obtained. The probe operation support information is provided to a user using a display device, a speaker, etc. Thus, because it is possible to provide, to a user, information for re-creating the past probe position and/or past probe orientation, the load to the user during a position adjustment process and/or an orientation adjustment process of the probe is reduced. In addition, it is possible to precisely identify a part which is diagnosed with ultrasound in the past.

In the above-described configuration, a probe is, for example, a probe for measuring two-dimensional data or a probe for measuring three-dimensional data. As the coordinate measuring unit, it is preferable to use a magnetic field measurement system as will be described below. Alternatively, it is also possible to use, as the coordinate measuring unit, a mechanical measurement system, an optical measurement system, a measurement system which uses electric waves, and a measurement system which uses ultrasound, for example. The magnetic field measurement system preferably has a magnetic field generator provided on one of the probe and a predetermined fixed location, a magnetic sensor provided on the other one of the probe and the predetermined fixed location, and a coordinate data calculator which calculates the coordinate data based on an output of the magnetic sensor. Typically, a magnetic sensor of a relatively small size is provided within the probe and a magnetic field generator of a relatively large size is provided on a fixed location near a bed.

In the above-described structure, it is possible to record a plurality of sets of recorded coordinate data in the coordinate storage unit and to select one of the recorded coordinate data from among the plurality of sets of recorded coordinate data, according to the subject and part to be diagnosed. The probe operation support information maybe information for supporting only one of the position adjustment operation and the orientation adjustment operation of the probe, but is preferably information for supporting both the position adjustment operation and the orientation adjustment operation of the probe. The probe operation support information can be provided through an image display, an acoustic output, an optical output, or one or a plurality of other means. The probe operation support information may be information spatially representing the recorded probe coordinate and the current probe coordinate or be information representing a relationship among the recorded probe coordinate and the current probe coordinate (such as, for example, difference and proximity direction).

According to another aspect of the present invention, it is preferable that, in the ultrasound diagnosis apparatus, the information generator unit generates the probe operation support information by comparing the recorded coordinate data and the current coordinate data. According to another aspect of the present invention, it is preferable that, in the ultrasound diagnosis apparatus, the probe operation support information contains a guidance display and the guidance display indicates at least one of match or proximity between the recorded coordinate data and the current coordinate data. According to another aspect of the present invention, it is preferable that, in the ultrasound diagnosis apparatus, the guidance display contains an indicator array indicating, for each coordinate component, a match and a proximity between the recorded coordinate data and the current coordinate data. According to another aspect of the present invention, it is preferable that, in the ultrasound diagnosis apparatus, the indicator array further indicates, for each coordinate component, a polarity of a direction of proximity.

According to another aspect of the present invention, it is preferable that, in the ultrasound diagnosis apparatus, the probe operation support information contains a reference image, and the reference image is an image which represents the recorded coordinate data and the current coordinate data in a three-dimensional coordinate system based on a subject. According to another aspect of the present invention, it is preferable that, in the ultrasound diagnosis apparatus, the reference image contains a recorded probe mark which is generated based on the recorded coordinate data and a current probe mark which is generated based on the current coordinate data. According to another aspect of the present invention, it is preferable that, in the ultrasound diagnosis apparatus, each of the recorded probe mark, the current probe mark, and the body mark is a three-dimensional image.

(2) According to another aspect of the present invention, there is provided an ultrasound diagnosis apparatus comprising a transportable probe which is operated by a user and which transmits and receives ultrasound and outputs received data, a coordinate measuring unit which measures a spatial position and orientation of the probe and outputs coordinate data representing a result of measurement, an instruction generator unit which generates a recording instruction, a coordinate storage unit which records recorded coordinate data at a timing in which the recording instruction is generated, an information generator unit which generates probe operation support information for approximating or matching, based on a comparison between the recorded coordinate data recorded in the coordinate storage unit and current coordinate data which is coordinate data currently output from the coordinate measuring unit, the current coordinate data to the recorded coordinate data, and an information provision unit which provides the probe operation support information to the user.

According to another aspect of the present invention, it is preferable that the ultra sound diagnosis apparatus further comprises a display device which displays a current ultrasound image and the probe operation support information. According to another aspect of the present invention, it is preferable that the ultrasound diagnosis apparatus further comprises a display device which displays a current ultrasound image, a past ultrasound image, and the probe operation support information. According to another aspect of the present invention, it is preferable that, in the ultrasound diagnosis apparatus, the probe operation support information contains a reference image, the reference image contains a first graphical object generated based on the recorded coordinate data and a second graphical object generated based on the current coordinate data, and the second graphical object moves corresponding to a movement of the probe. According to another aspect of the present invention, it is preferable that, in the ultrasound diagnosis apparatus, the probe operation support information contains a guidance display, and the guidance display indicates a relationship between the recorded coordinate data and the current coordinate data for each coordinate component.

It is preferable to execute calibration before coordinate measurement in order to define a coordinate system which reflects the size and orientation of the subject. In the calibration, an operation is performed to adjust the size and scale of the body mark to conform with the actual size and scale of the subject. As a result of this process, it is possible to generate a reference image which accurately reflects the position of the probe (actual measurement part) on the subject. In the calibration, a method is preferably used in which a center position on the transmission/reception surface of the probe is sequentially contacted with a plurality of parts on the subject for calibration which are set in advance and the size of the subject is measured (alternatively, it is also possible to use a method as described in Japanese Patent Application No. 2002-218497 which is not made public at the time of filing of a Japanese patent application for the present invention).

BRIEF DESCRIPTION OF THE DRAWINGS

A preferred embodiment of the present invention will be described in detail based on the following figures, wherein.

DESCRIPTION OF PREFERRED EMBODIMENT

A preferred embodiment (hereinafter referred to simply as "embodiment") of the present invention will now be described.

Figure 1:
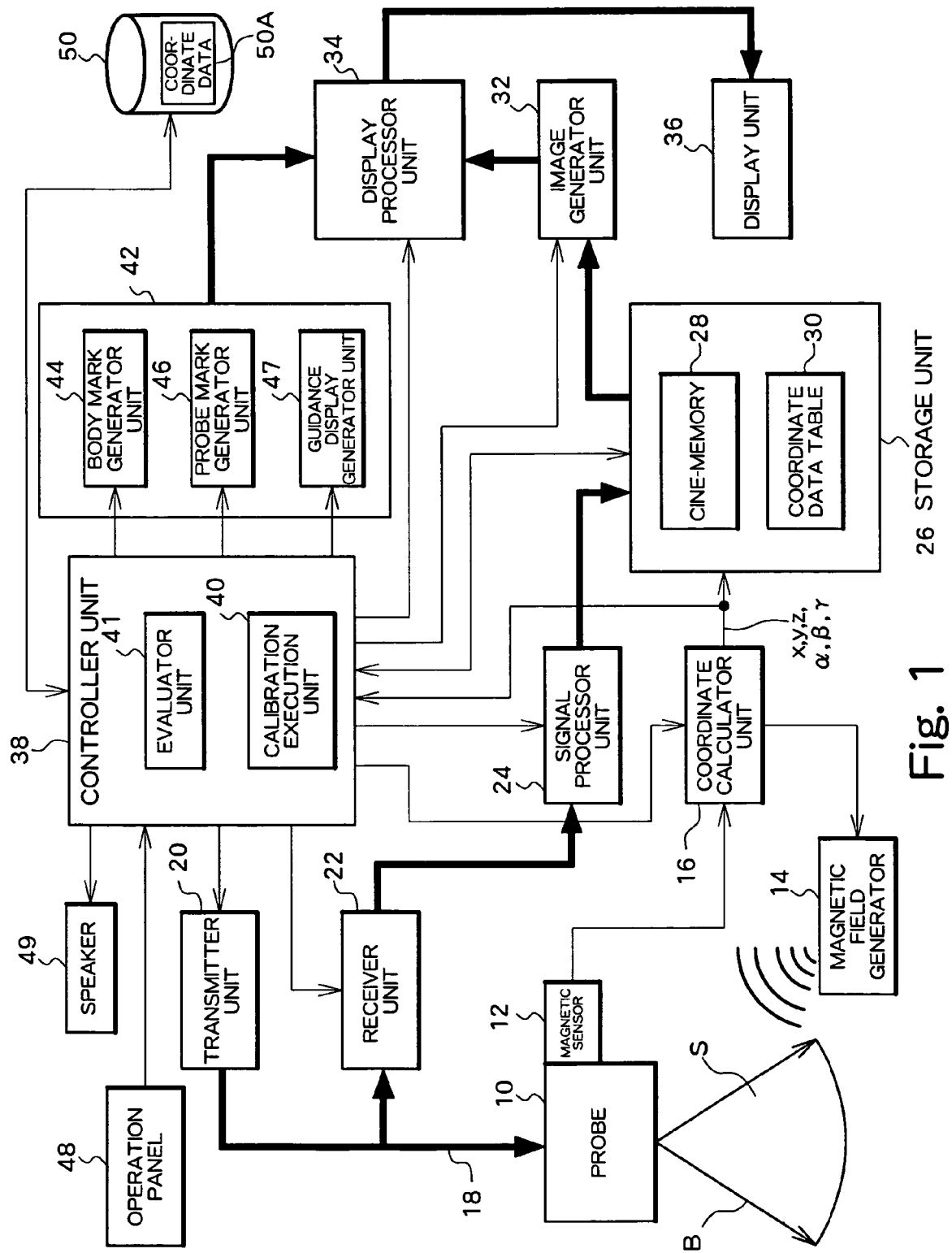
FIG. 1 is a block diagram showing an overall structure of an ultrasound diagnosis apparatus according to a preferred embodiment of the present invention.

FIG. 1 is a block diagram showing an overall structure of an ultrasound diagnosis apparatus according to a preferred embodiment of the present invention. As will be described later, the ultrasound diagnosis apparatus has a function to display a reference image, a function to display a guidance display, etc. for supporting operations of the probe by the user.

A probe 10 is a transportable device for transmitting and receiving ultrasound. The probe 10 has a transducer array including a plurality of transducer elements in the structure exemplified in FIG. 1. The transducer array generates an ultrasound beam B. By electronically scanning with the ultrasound beam B, a two-dimensional scanning plane S is generated. As a method of electronic scanning, it is possible to employ, for example, an electronic sector scanning system or an electronic linear scanning system. It is also possible to provide a 2D (two-dimensional) transducer array in the probe 10 to form a 3D (three-dimensional) data obtaining space.

An ultrasound diagnosis apparatus according to the embodiment comprises, as means for measuring coordinates, a magnetic field generator 14, a magnetic sensor 12, and a coordinate calculator unit 16. In the configuration shown in FIG. 1, the magnetic field generator 14 is provided at a predetermined fixed location, such as a position near a bed (not shown) on which a patient is located. The magnetic sensor 12, on the other hand, is provided on the probe 10 in the example configuration of FIG. 1. More specifically, the magnetic sensor 12 is stored and located within a resin case in the probe 10. Various devices may be used as the magnetic field generator 14 and the magnetic sensor 12, as long as these devices can measure a three-dimensional position and a three-dimensional orientation of the probe 10. The magnetic field generator 14 has, for example, three magnetic field generator coils provided corresponding to three axes which are perpendicular to each other. These three coils are driven in a time divisional manner. The magnetic sensor 12 comprises, for example, three magnetic filed detector coils provided corresponding to three axes which are perpendicular to each other. The coordinate calculator unit 16 calculates a spatial position (x, y, z) of the probe 10 and a rotational angle ($\alpha$, $\beta$, Y) of the probe 10 with respect to the axes based on output signals of the coils output from the magnetic sensor 14. The coordinate measurement technique itself is a known technique. The definition of the components of the coordinate system may be other than those described above.

The probe 10 is connected to a main system of the apparatus through a cable 18. That is, the probe 10 in the embodiment is transportable and is, in general, used in contact with a surface of the body of the subject. Alternatively, it is also possible to use a probe 10 which is inserted into a body orifice, such the esophagus.

A structure of the main system of the apparatus will now be described. A transmitter unit 20 functions as a transmission beam former. The transmitter unit 20 supplies, to the plurality of transducer elements, a plurality of transmission signals to which a delay process is applied, under the control of a controller unit 38. A receiver unit 22 functions as a reception beam former. The receiver 22 applies a phase adjusting and summing process to a plurality of reception signals output from the plurality of transducer elements under a control of the controller unit 38.

A signal processor unit 24 applies processes such as detection and logarithmic compression to the phase adjusted and summed reception signal output from the receiver unit 22. These processes may alternatively be applied downstream of a storage unit 26 which will be described below. In this configuration, an RF signal is stored in the storage unit 26. The storage unit 26 stores reception signal (received data) before coordinates are converted. Alternatively, it is also possible to store, in the storage unit 26, received data after coordinates are converted.

In the embodiment, the storage unit 26 has a cine-memory 28 and a coordinate data table 30. The cine-memory 28 stores received data of a plurality of frames which are input in time series. The cine-memory 28 has a storage structure similar to a ring buffer. The cine-memory 28 always stores a sequence of received data from a most recent frame to a frame of a predetermined time before. As is known, when a user applies a freeze operation, transmission and reception of the ultrasound is terminated. At this point, the stored content in the cine-memory 28 is frozen. When an ultrasound image is to be displayed in real time, it is possible to employ a configuration in which received data output from the signal processor unit 24 is temporarily stored in the cine-memory 28 and the received data is immediately read from the cine-memory 28. Alternatively, it is also possible to output the received data output from the signal processor unit 24 directly to an image generator unit 32 which will be described later and, at the same time, store the received data in the cine-memory 28.

The coordinate data table 30 is a table which stores a plurality of coordinate data correlated to a plurality of received data stored in the cine-memory 28. When certain received data is stored in the cine-memory 28, coordinate data correlated to the received data is stored in the coordinate data table 30. The coordinate data represents a position and an orientation of the probe 10 at the time when the received data is obtained. In the present embodiment, one item of coordinate data is correlated to and stored with one item of received data. Therefore, similar to the cine-memory 28, the coordinate data table 30 also has a storage structure similar to a ring buffer.

The management unit of the received data in the cine-memory 28 may be, for example, beams, frames, or volumes. The management unit of coordinate data in the coordinate data table 30 may also be a unit such as beams, frames, or volumes, similar to the management unit of the received data. In the present embodiment, the correlation between the received data and the coordinate data is managed with one frame composed of a plurality of beams as the management unit, Alternatively, in this configuration, one coordinate data may be correlated to a plurality of received data. Alternatively, a plurality of coordinate data may be correlated to one received data. In the present embodiment, the coordinate data is formed as a set of parameter values of x, y, z, $\alpha$, $\beta$, and Y, as already described above. Among these parameters, measurement and storage of, for example, known values or constant values may be omitted. Alternatively, it is also possible to form the coordinate data with only parameter values, among the six parameter values, necessary for generation of the reference image. In any case, because the coordinate data is correlated to and stored with the received data, it is possible to use the coordinate data correlated to the received data when the received data is replayed, as will be described later. In other words, the present embodiment has an advantage that the body mark and the probe mark can be automatically generated and displayed using the coordinate data. Control to write data and control to read data to and from the storage unit 26 are executed by the controller unit 38 which will be described later. It is also possible to store an electrocardiographic signal in the cine-memory 28 along with the received data.

In the present embodiment, coordinate data of past diagnoses is separately stored as recorded coordinate data, and probe operation support information, described later, is generated using the recorded coordinate data.

The image generator unit 32 is means for generating an ultrasound image as a living body image based on the received data and has, for example, a digital scan converter (DSC). In the present embodiment, a two-dimensional ultrasound image (image of tissue and image of blood stream, etc.) are generated. Alternatively, a three-dimensional image may be generated or an M mode image or a Doppler waveform image may be generated.

A display processor unit 34 synthesizes image data as living body image output from the image generator unit 32 and graphical data output from a graphics generator unit 42 which will be described below and outputs data which represents a synthesized image. The image data output from the display processor unit 34 is sent to a display unit 36. A synthesized image including the living body image and the graphical image is displayed on a screen of a display unit 36.

The graphical image contains a reference image. In the present embodiment, the reference image contains a body mark and one or a plurality of probe marks. In the present embodiment, it is possible to display a recorded or registered probe mark along with a current probe mark as necessary. As will be described in more detail later, the recorded probe mark is a graphical object generated based on the recorded coordinate data (graphical object re-creating a past position and a past orientation of the probe during past examination). The current probe mark is a graphical object generated based on the current coordinate data (graphical object representing a current position and a current orientation of the probe). By simultaneously displaying the recorded probe mark and the current probe mark, it is possible to quickly and easily match the current position and the current orientation of the probe to the position and the orientation of the probe during the past examination. In particular, when a past ultrasound image and a current ultrasound image are to be display side by side using a two-screen display function, such a reference image is used as the probe operation support information. In addition, a guidance display which will be described later is also used as the probe operation support information.

The display unit 36 may alternatively be formed with two display devices (main display device and auxiliary display device). In this configuration, the living body image may be displayed on one of the two display devices and the graphical image may be displayed on the other of the two display devices. The synthesized image can be recorded on a recording medium such as a VTR and CD-ROM, printed on paper, or captured as a photograph. Because the synthesized image contains the reference image, it is possible to record the reference image along with the living body image.

The controller unit 38 has a CPU for executing software instructions. The controller unit 38 controls operations of the structures shown in FIG. 1 and, in particular, supplies a graphics generation condition to the graphics generator unit 42 which is substantially formed by a software.

The controller unit 38 has a calibration function, here embodied within a calibration execution unit 40. A calibration process is executed before measurement in order to correlate (conform) a scale or a size in the body mark to a real scale or a real size in the subject by identifying a coordinate system in the subject.

When one part of one patient is to be repeatedly examined with ultrasound, it is desirable to execute, in each examination, calibration before the actual ultrasound measurement. With this configuration, it is possible to accurately match the coordinate system in the past examination and the coordinate system of the current examination. As a result, even when the position or the orientation of the patient lying on the bed differ between the past examination and the current examination, it is possible to provide, to the user, probe operation support information in the current examination according to the corrected coordinate system.

A specific example of calibration will now be described. In the present embodiment, with an operation by the user, a center position of a transmission/reception surface of the probe 10 is contacted to a plurality of specific positions for calibration defined on the subject and coordinate data of the probe is obtained at each of the specific positions. A coordinate system in the subject is then identified based on the plurality of coordinate data corresponding to the plurality of specific positions. According to this identification, it is possible to conform the coordinate system with respect to the body mark to the coordinate system with respect to the subject. The conforming of coordinate systems includes matching of origins, matching of the scales or sizes, etc. When mismatch of coordinate systems between the subject and the body mark does not pose a problem, it is not necessary to apply the calibration process.

When the calibration process as described above is executed, a result of the calibration is supplied from the controller unit 38 to the coordinate calculator unit 16. In an ultrasound diagnosis after the calibration, the coordinate calculator unit 16 calculates the probe coordinates based on an output signal of the magnetic sensor 12 and according to a coordinate system based on the subject defined through the calibration. The coordinate calculator unit 16 outputs the coordinate data which is the result of the calculation, to the coordinate data table 30 of the storage unit 26 and also to the controller unit 38. The controller unit 38 receives the coordinate data output from the coordinate calculator unit 16 when the ultrasound image is to be displayed in real time. When, on the other hand, an image is to be replayed using the cine-memory 28, the controller unit 38 receives coordinate data read from the coordinate data table 30. The controller unit 38 controls generation of the body mark and generation of the probe mark based on the received coordinate data, as will be described below. In the present embodiment, the three-dimensional body mark and the three-dimensional probe mark can be automatically displayed both in a configuration in which the ultrasound image is to be displayed in real time (real time display mode) and in a configuration in which the ultrasound image is to be replayed and displayed using received data which is stored in the cine-memory functioning as a storage device (replay display mode).

In the present embodiment, the controller unit 38 comprises an evaluator unit 41. The evaluator unit 41 evaluates proximity, proximity direction, and match, by comparing the recorded coordinate data and the current coordinate data. The controller unit 38 reads coordinate data output from the coordinate calculator unit 16 at a timing in which an explicit instruction is given by the user or at a timing when a predetermined condition is satisfied and stores the read coordinate data to an external storage device 50 as recorded coordinate data 50A. Alternatively, the controller unit 38 stores, during the period when an ultrasound image is replayed and a specific ultrasound image is selected and stored for examination report, coordinate data corresponding to the specific ultrasound image to the external storage device 50 as the recorded coordinate data 50A. With this configuration, coordinate data read from the coordinate data table 30 is utilized. It is also possible to store the recorded coordinate data 50A to a storage device different from the external storage device 50. The recorded coordinate data represents a position and an orientation of the probe during the past examination. The evaluator unit 41 compares the stored recorded coordinate data and the current coordinate data which is currently obtained in real time and outputs a result of comparison to a guidance display generator unit 47 provided in the graphics generator unit 42. In addition, the evaluator unit 41 uses a speaker 49 to notify, with a predetermined sound, the user of information such as proximity and matching, based on the result of comparison. This configuration is one form of provision of the probe operation support information.

In the example of the present embodiment, the graphics generator unit 42 comprises a body mark generator unit 44, a probe mark generator unit 46, and a guidance display generator unit 47. These generator units 44 and 46 are substantially realized by software in the present embodiment. In the generator units 44 and 46, a mark corresponding to the condition output by the controller unit 38 is selected from among a plurality of marks which are provided in advance or a mark is generated based on the condition output by the controller unit 38 when the controller unit 38 outputs the condition. In the present embodiment, the body mark generator unit 44 generates a monochrome or color three-dimensional body mark and the probe mark generator unit 46 generates a monochrome or color three-dimensional probe mark (recorded probe mark and current probe mark). The body mark and the probe mark may alternatively be digital images captured by a digital camera.

The guidance display generator unit 47 generates a guidance display reflecting a result of evaluation in the evaluator unit 41. An example of this display will be described later. In the present embodiment, the guidance display contains a plurality of indicators corresponding to a plurality of coordinate components forming the coordinate data. More specifically, the plurality of indicators correspond to all or a portion of coordinate components of x, y, z, α, β, and Y. In the present embodiment, each indicator executes a display operation for identifying three forms of proximity in a positive direction, matching, and proximity in a negative direction. This display operation will be described later referring to FIG. 5, etc. Alternatively, it is also possible to employ a configuration in which each indicator only displays matching.

In the present embodiment, the graphics generator unit 42 functions both in the real time display mode and replay display mode. In other words, in both display modes, the body mark and the probe mark can be automatically generated according to a display condition output from the controller unit 38. Graphical data containing these marks is supplied to the display processor unit 34. The display processor unit 34 executes a process to synthesize the living body image data and the graphical data and supplies the data of the synthesized image generated in this process to the display unit 36.

More specifically, the body mark generator unit 44 can generate a plurality of types of body marks. More specifically, the body mark generator unit 44 can generate a three-dimensional body mark having a suitable form corresponding to the diagnosis item, diagnosis part, type of patient, and size of patient. Information indicating the type of body mark is stored in the coordinate data table 30 as will be described below. The probe mark generator unit 46, on the other hand, can generate a plurality of types of probe marks. More specifically, the probe mark generator unit 46 can generate a three-dimensional probe mark having a shape corresponding to the type of probe. Information indicating the type of the probe mark is stored in the coordinate data table 30 as will be described later. It is also possible to allow the direction for displaying the body mark (direction of view line) to be variable. The position and orientation of the probe mark is adaptively set based on the actual position and orientation of the probe. On the display screen, the probe mark is displayed overlapping the body mark. In this manner, the actual usage state of the probe is simulated and re-created on the display screen. In order to automatically generate a three-dimensional mark, it is possible to employ a known three-dimensional image constructing method such as, for example, volume rendering and surfacing method.

An external storage device 50 is connected to the controller unit 38 and stores various data necessary for control of operations by the controller unit 38. In addition, an operation panel 48 is connected to the controller unit 38. A user can set and input various parameters using the operation panel 48.

In the present embodiment, the external storage device 50 stores one or a plurality of sets of recorded coordinate data. The plurality of sets of recorded coordinate data are managed, for example, for each subject and for each diagnosis part and one set of recorded coordinate data is selected by specifying a subject and a diagnosis part. It is also possible to employ a configuration in which one of the coordinate data stored in the coordinate data table 30 is used as the recorded coordinate data. The user can input a recording instruction of coordinate data using the operation panel 48. In addition, using the operation panel 48, the user can input an instruction for storing one of the ultrasound images (or received data for generating the ultrasound image) as an ultrasound image for examination report. It is also possible to employ a configuration in which, when this instruction is input, the coordinate data correlated to the ultrasound image to be stored is automatically stored as the recorded coordinate data. When a stored past ultrasound image is replayed and displayed for a comparison purpose, the recorded coordinate data correlated to the ultrasound image is identified and user operation support information is generated based on the recorded coordinate data. For this purpose, a correlation relationship between the ultrasound image to be stored and the recorded coordinate data is managed. The ultrasound image can be stored in the storage unit 26, the external storage device 50, or any other storage medium.

Figure 2:
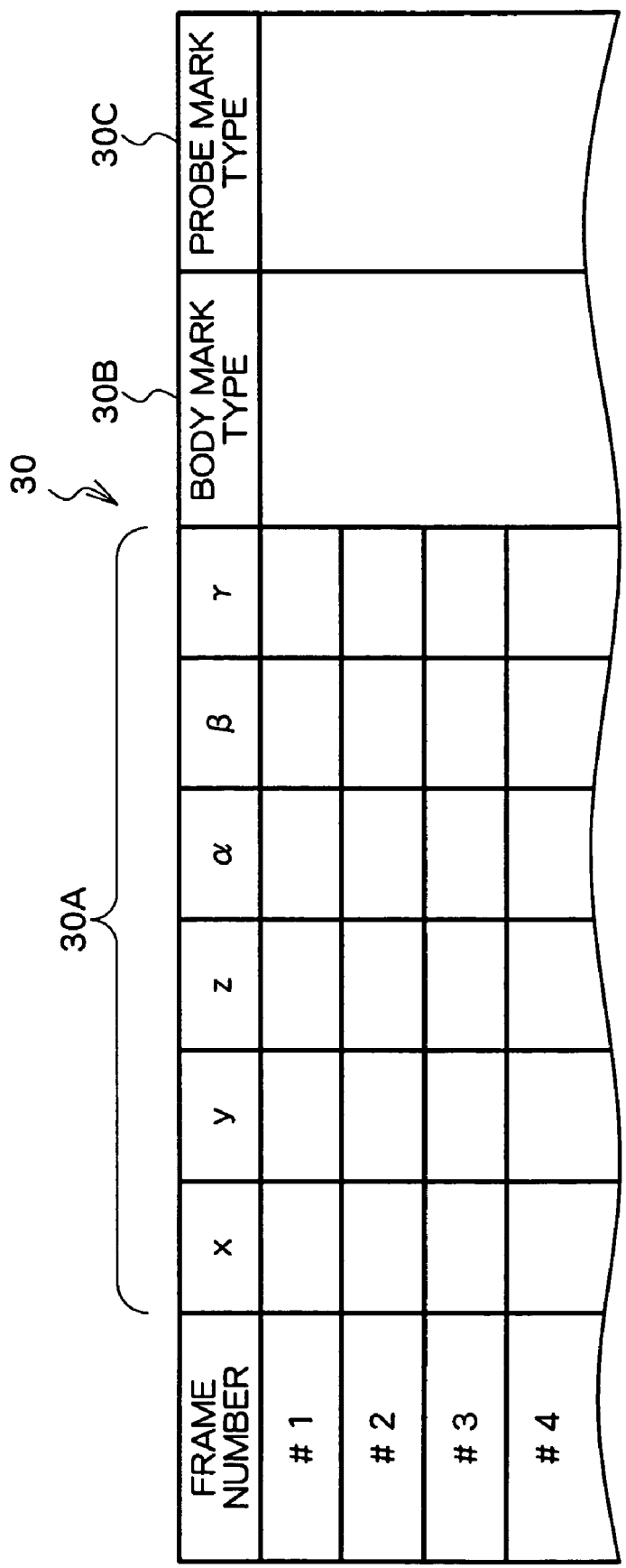
FIG. 2 is a diagram showing an example of a specific structure of a coordinate data table shown in FIG. 1.

FIG. 2 shows a specific example structure of the coordinate data table 30 shown in FIG. 1. In the structure exemplified in FIG. 2, the received data is managed in units of frames. Specific coordinate data 30A is correlated to the frame number. The coordinate data is made of data x, y, and z representing the spatial position of the probe and data α, β, and Y presenting the orientation of the probe. This configuration, however, is only exemplary, and coordinate data of various forms may be used as long as the coordinate data allows appropriate display of the marks.

In the present embodiment, the coordinate data table 30 stores body mark type information 30B and probe mark type information 30C in addition to the coordinate data. The type of the body mark is automatically selected based on medical information and patient information or is selected by the user. The type of the probe mark is automatically identified or is registered by the user. Because the information 30B and 30C are stored in the coordinate data table, the types of marks can be automatically selected using the information 30B and 30C both in the real time display mode and in the replay display mode. Alternatively, it is also possible to employ a configuration in which the user designates one or both of the body mark type and the probe mark type after the freeze operation as necessary.

Figure 3:
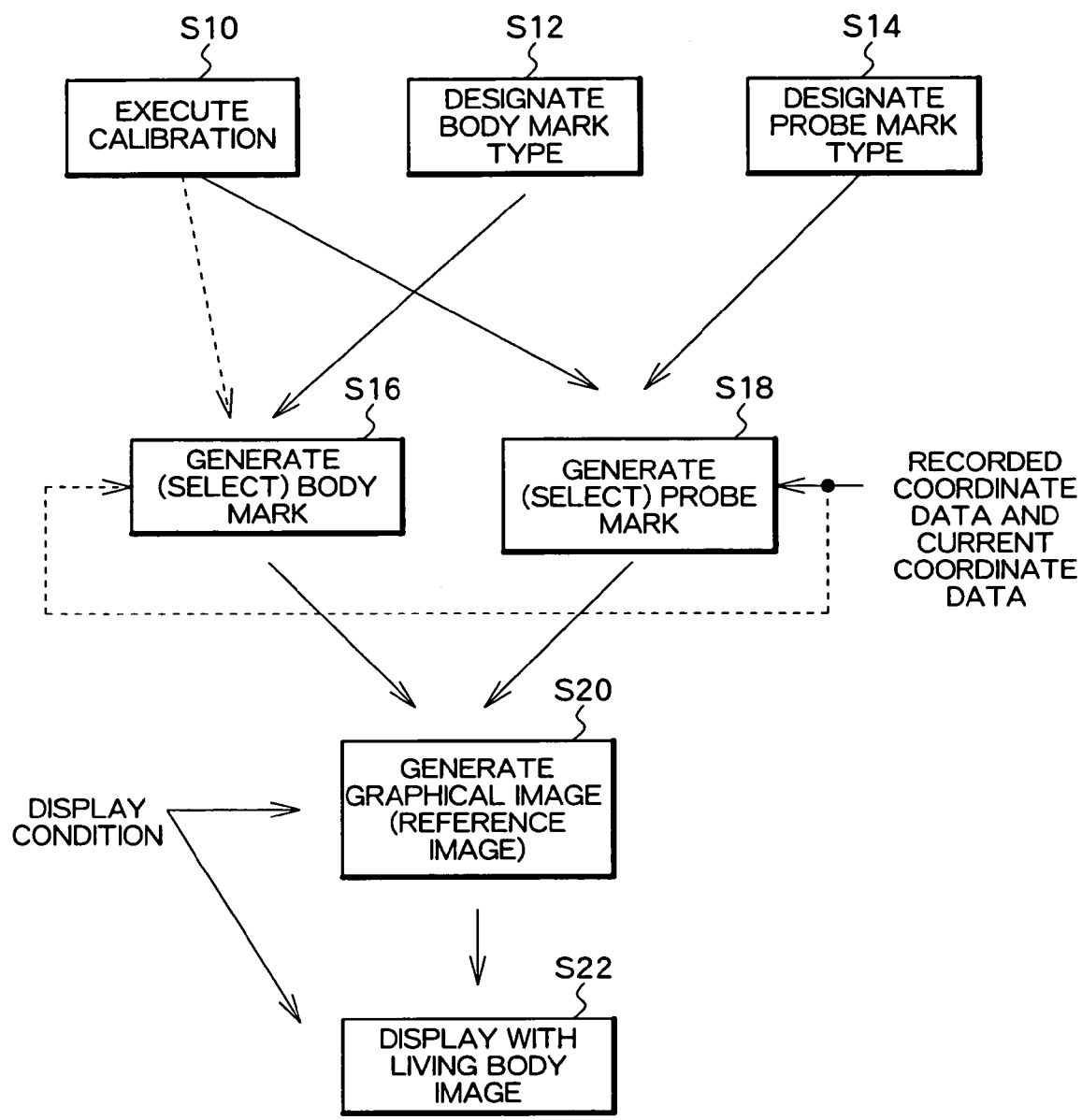
FIG. 3 is a conceptual diagram for explaining a generation process of a reference image.

FIG. 3 is a conceptual diagram showing a process for generating a reference image. This example process shows a procedure for generating a reference image for matching a position and an orientation of a probe in current examination (that is, current diagnosis part) to a position and an orientation of a probe in a past examination (that is, past diagnosis part). When the ultrasound image is displayed in real time or when the ultrasound image is replayed and displayed using a cinememory also, a reference image is generated basically through the process shown in FIG. 3.

Step S10 indicates a calibration step in the past examination and in the current examination. Either prior to or following the calibration, in step S12, a body mark type is designated and, in step S14, a probe mark type is designated. The mark types are designated automatically or by the user. In this configuration, it is preferable that a control is applied such that the body mark type and the probe mark type designated in the past examination are automatically selected in the current examination. In step S16, a body mark is generated and, in step S18, a recorded probe mark and a current probe mark are generated. In this process, the recorded probe mark is generated based on the recorded coordinate data as described above. More specifically, the recorded probe mark is generated such that the recorded probe mark is synthesized on the body mark at a position indicated by the recorded coordinate data and with an orientation indicated by the recorded coordinate data. The current probe mark is generated in real time based on the coordinate data currently obtained in real time. More specifically, the current probe mark is generated such that the current probe mark is synthesized on the same body mark at a position indicated by the current coordinate data and with an orientation indicated by the current coordinate data. In this configuration, it is preferable to apply a display process to allow visual distinction between the recorded probe mark and the current probe mark. For example, it is possible to use a different brightness, different color, or the like between the probe marks. The recorded probe mark maybe a simulation of the actual form of the probe, or, alternatively, may be represented by a mark or a symbol such as an arrow indicating the position of contact and direction of contact of the probe.

In the above-described step S18, the recorded probe mark and current probe mark are generated according to a probe mark type designated in step S14. In this process, results of execution of the calibration in the past examination and in the current examination are considered. Similarly, in the above-described step S16, the body mark is generated based on the body mark type designated in step S12. In this process, results of execution of the calibration in the past examination and in the current examination are considered and the recorded coordinate data and the current coordinate data are considered as necessary. For example, a specific body mark is selected from among a plurality of body marks belonging to the designated body mark type, according to the current coordinate data.

In step S20, a graphical image (reference image) is generated by synthesizing the body mark (graphical data) and the recorded probe mark and the current probe mark (graphical data). More specifically, the reference image is generated according to the display condition. For example, a color coding process of skin color may be applied to the body mark and a color coding process reflecting the actual colors of the probe may be applied to the recorded probe mark and the current probe mark. In step S22, a graphical image (that is, a reference image) is displayed on the screen along with the living body image according to the display condition which is set by the controller unit.

The above-described processes are executed for each frame. For example, when the received data from the cinememory is to be displayed as an animation image, the movement of the probe when the received data is obtained is re-created as the movement of the probe mark.

Figure 4:
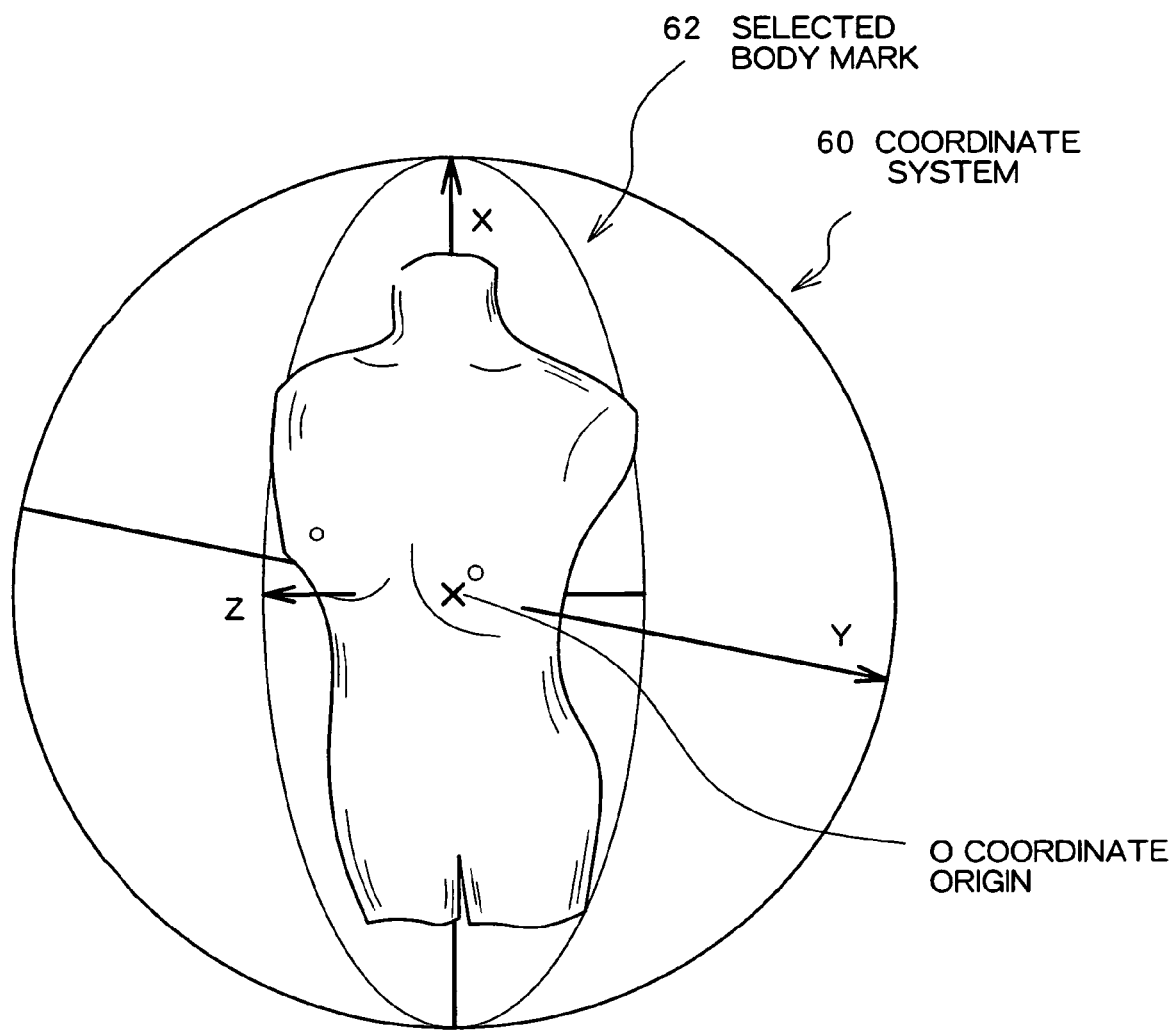
FIG. 4 is a diagram for explaining a coordinate system defined through calibration.
Figure 5:
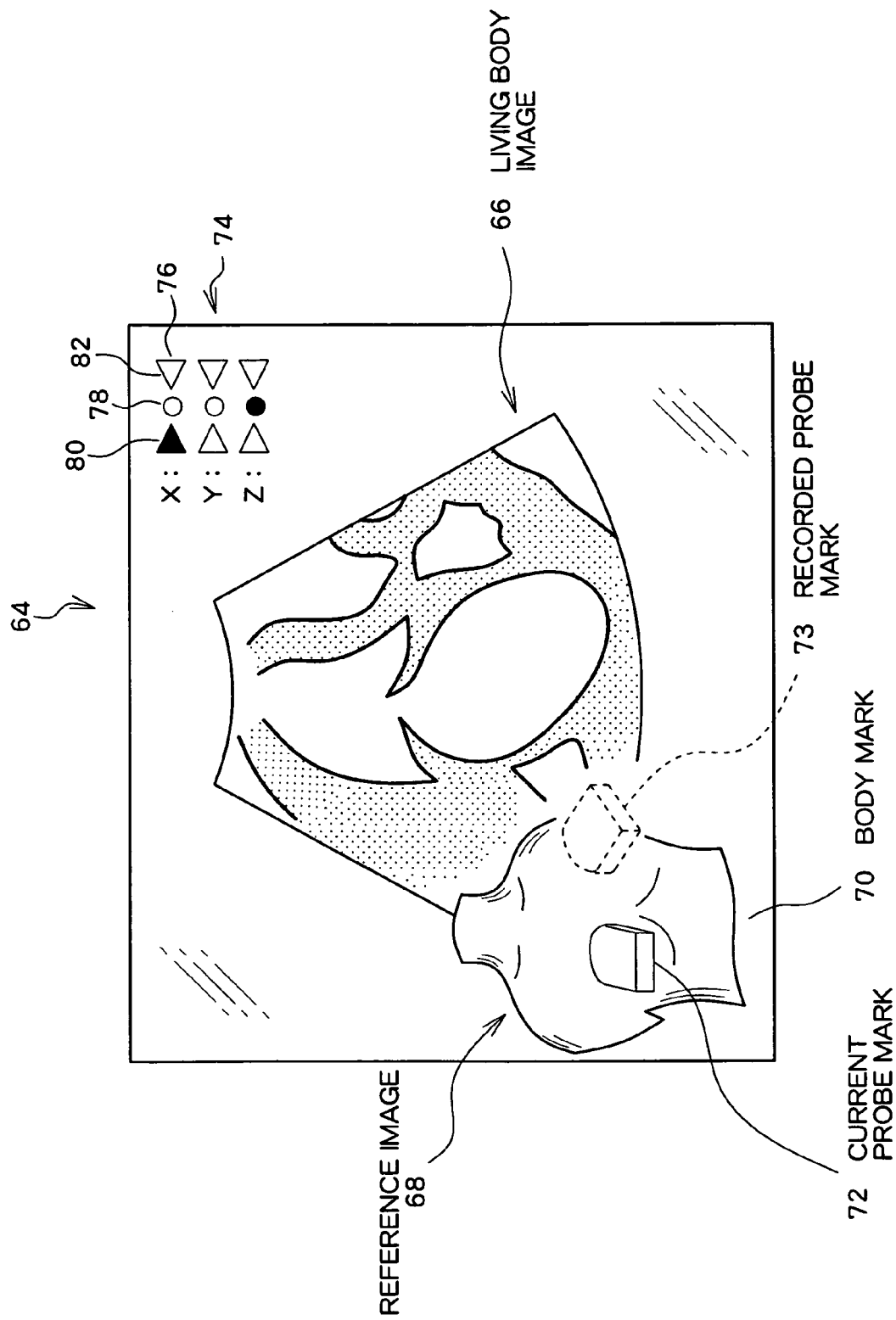
FIG. 5 is a diagram for explaining a reference image, a living body image, and a guidance display.

FIG. 4 shows a coordinate system 60 defined regarding the body mark (or the subject). The coordinate system 60 is defined in the calibration process described above. FIG. 4 shows a typical body mark 62. The coordinate system 60 has three perpendicular axes X, Y, and Z which pass though a coordinate origin O. The position and orientation of the probe in such coordinate system 60 is measured in real time by the above-described coordinate measuring means. It is also possible to three-dimensionally display, on the screen, the coordinate system as shown in FIG. 4 to achieve a representation to allow comparison between the position and orientation of the probe (or diagnosis part) during past examination and the current position and the current orientation of the probe (or diagnosis part). FIG. 5 shows an example of a display screen 64. A living body image 66 and a reference image 68 are shown on the display screen 64. As described above, the reference image 68 includes a body mark 70, a recorded probe mark 73, and a current probe mark 72. These marks are three-dimensional images having a perceived depth. The recorded probe mark 73 re-creates the position and the orientation of the probe in the past diagnosis and is displayed on the body mark 70 at a position based on the recorded coordinate data and with an orientation based on the recorded coordinate data. In the example illustrated in FIG. 5, the recorded probe mark 73 is represented as a halftone image such that the recorded probe mark 73 is visually distinguishable from the current probe mark which is displayed with a normal brightness. The current probe mark 72 represents the current position and the current orientation of the probe and is displayed on the body mark 70 at a position based on the current coordinate data and with an orientation based on the current coordinate data. When the contact position of the probe is moved on the subject or the contact orientation of the probe is changed on the subject, the position or the orientation of the current probe mark is changed corresponding to the movement of he probe. With such a structure, the user can change the contact position and contact orientation of the probe to match the current probe mark 72 to the recorded probe mark 73 to easily approximate or match the diagnosis part in the current diagnosis to the diagnosis part in the past diagnosis. When the past ultrasound image (still image) and the current ultrasound image (real time image) are simultaneously displayed using a two-screen display function also, it is desirable to display the reference image 68.

A display position of the reference image 68 on the display screen 64 can be arbitrarily set by the user. It is desirable to allow the user to arbitrarily set the size of the reference image. Alternatively, it is also possible to prepare a plurality of body marks representing the same part and having different directions and to automatically select the body mark to be displayed according to the position of the probe. It is also possible to allow generation of a plurality of body marks which can represents the state of a patient lying on a bed.

The reference image as described above is one form of probe operation support information. In the present embodiment, other probe operation support information may be provided. Specifically, as will be described below, it is also possible to provide a guidance display which notifies that the current coordinate data becomes close to or matches the recorded coordinate data.

A guidance display 74 shown on FIG. 5 has an indicator array having three indicators 76 corresponding to three coordinate components. Specifically, the indicator array has three indicators 76 corresponding to the three coordinate components of X, Y, and Z. Each indicator 76 has a pair of triangular elements 80 and 82 which oppose each other in orientations opposite to each other and a circular element 78 provided between the triangular elements 80 and 82. For example, regarding the X coordinate, when the current X coordinate of the probe becomes close to the recorded X coordinate, the triangular element corresponding to the closing direction is displayed with a higher brightness. With this configuration, it is possible to recognize that the probe is close in the X direction and the closing or proximate direction. When the current X coordinate of the probe matches the recorded X coordinate, the circular element at the center is displayed with a higher brightness. With this configuration, it is possible to notify that the coordinates match with respect to the X direction. This operation is also similarly applied in the Y and Z directions.

The indicator array shown in FIG. 5 is for evaluating the current probe position. An additional indicator array may be provided for evaluating the current probe orientation. In either case, with the guidance display 74, the user can be notified of the direction and an amount of movement the probe should be moved in real time. With either configuration, it is possible to quickly and easily match the current diagnosis part to the past diagnosis part and there is an advantage that the matched state can be visually and easily confirmed. The illustrated guidance display of FIG. 5 is only exemplary and other display forms may be employed. In the present embodiment, when matching is achieved for all coordinate components, a predetermined sound is output and recording, etc. of the ultrasound image is performed manually or automatically when the sound is output.

When the same diagnosis part of the same subject is examined two or more times, or when the past ultrasound image and the current ultrasound image are displayed side by side in a two-screen display, it is possible to support the probe operations of the user by displaying the reference image and/or providing the guidance display as described above.

Figure 6:
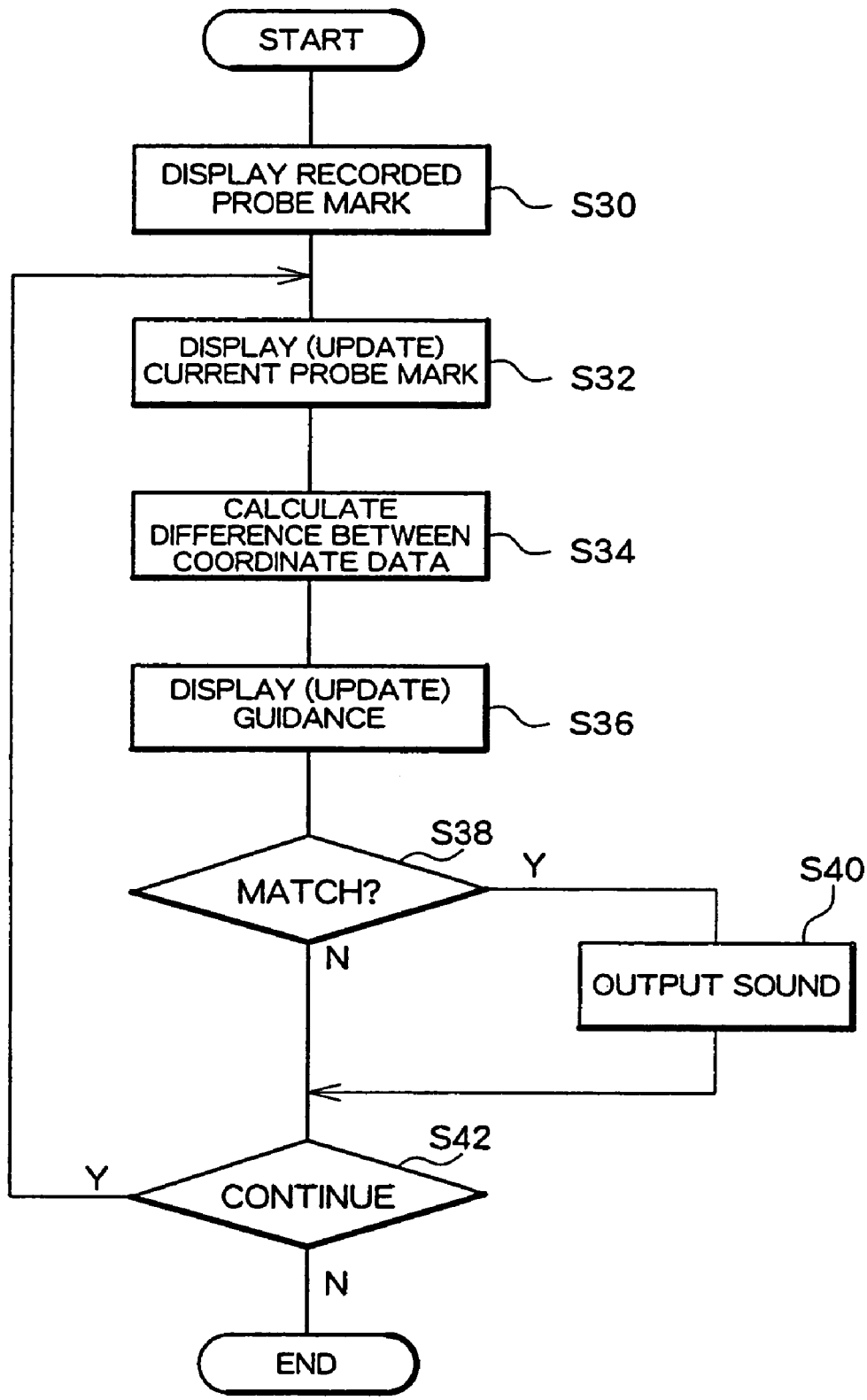
FIG. 6 is a flowchart showing an operation of the apparatus shown in FIG. 1.

FIG. 6 shows a flowchart of an operation to provide probe operation support information. In steps S30 and S32, a recorded probe mark and a current probe mark are displayed. These steps are normally executed simultaneously, but are shown in FIG. 6 as separate steps for purposes of explaining the operation. In step S34, recorded coordinate data and current coordinate data are compared and a difference value is calculated for each coordinate component. In step S36, a guidance display is generated based on these difference values or the content of the guidance display which is already displayed is updated. When an exact match is determined between the past diagnosis part and the current diagnosis part in step S38, a predetermined sound is output in step S40. When, on the other hand, an exact is not determined, the process jumps from step S42 back to step S32 and the steps described above are repeated. That is, the display position and display orientation of the current probe mark are changed in real time according to coordinate data measured in real time (step S32) and the display content (form of display of the indicator for each coordinate component) of the guidance display is updated according to a result of difference calculation which is calculated in real time. The user can easily match the current probe position and orientation to the recorded probe position and orientation by observing the reference image and the guidance display. A sound is output in step S40 when an exact match is achieved, and the image recording process is automatically or manually executed at that point. When another recorded coordinate data is selected, the sequence of steps from the step S30 is executed in a manner similar to that described above.

The probe operation support information generated based on the recorded coordinate data and the current coordinate data is not limited to that described above. It is also possible, for example, to configure to allow a plurality of types of probe operation support information to be generated and allow the user to select one or a plurality of information from among these information.

According to the present embodiment, probe operations by a user are supported and a load of the user can be reduced. In addition, it is possible to quickly match or approximate the current diagnosis part to the past diagnosis part. An appropriate evaluation and an appropriate diagnosis can be provided based on a comparative observation of the past ultrasound image and the current ultrasound image.

What is claimed is:

1. An ultrasound diagnosis apparatus comprising:
   an ultrasonic probe which transmits and receives ultrasound and outputs received ultrasonic data;
   a coordinate measuring unit which measures at least one of a spatial position and orientation of the ultrasonic probe and outputs coordinate data representing a result of measurement for the ultrasonic probe;
   a coordinate storage unit which recorded coordinate data;
   an information generator unit which generates probe operation support information based on the recorded coordinate data recorded in the coordinate storage unit and current coordinate data which is coordinate data currently output from the coordinate measuring unit; an information provision unit which provides the probe operation support information to a user;
   an ultrasound image generator which generates a current ultrasound image based on the received ultrasonic data;
   a display device which displays the current ultrasound image and the probe orientation support information; and wherein:
   the probe operation support information contains a guidance display, and the guidance display indicates at least one of match and proximity between the recorded coordinate data and the current coordinate data;
   the information generator unit generates the probe operation support information by comparing the recorded coordinate data and the current coordinate data; and
   the guidance display contains an indicator array indicating, for each coordinate component, a match and a proximity between the recorded coordinate data and the current coordinate data; and wherein
   the indicator array comprises a plurality of indicators corresponding to a plurality of coordinate components; and
   each of the plurality of indicators includes an indicator element indicating the match, an indicator element indicating the proximity in one direction, and an indicator element indicating the proximity in the other direction.

2. An ultrasound diagnosis apparatus according to claim 1, wherein the indicator array further indicates, for each coordinate component, a polarity of a direction of proximity.

3. An ultrasound diagnosis apparatus according to claim 1, wherein the probe operation support information contains a reference image, and the reference image is an image which represents the recorded coordinate data and the current coordinate data in a three-dimensional coordinate system based on a subject.

4. An ultrasound diagnosis apparatus according to claim 3, wherein the reference image contains a recorded probe mark which is generated based on the recorded coordinate data and a current probe mark which is generated based on the current coordinate data.

5. An ultrasound diagnosis apparatus according to claim 4, wherein the reference image further contains a body mark representing the subject.

6. An ultrasound diagnosis apparatus according to claim 5, wherein each of the recorded probe mark, the current probe mark, and the body mark is a three-dimensional image.

7. An ultrasound diagnosis apparatus comprising:
- a transportable ultrasonic probe which operated by a user and which transmits and receives ultrasound and outputs received ultrasonic data;
- a coordinate measuring apparatus unit which measures a spatial position and orientation of the ultrasonic probe and outputs coordinate data representing a result of the measurement;
- an instruction generator unit which generates a recording instruction;
- a coordinate storage unit which records recorded coordinate data at a timing in which the recording instruction is generated;
- an information generator unit which generates probe operation support information for approximating or matching, based on a comparison between the recorded coordinate data recorded in the coordinate storage unit and current coordinate data which is coordinate data currently output from the coordinate measuring unit, the current coordinate data to the recorded coordinate data;
- an information provision unit which provides the probe operation support information to the user;
- an ultrasound image generator which generates a current ultrasound image based on the received ultrasonic data;
- a display device which displays the current ultrasound image and the probe operation support information; and wherein:
- the probe operation support information contains a guidance display, and the guidance display indicates at least one of match and proximity between the recorded coordinate data and the current coordinate data;
- the information generator unit generates the probe operation support information by comparing the recorded coordinate data and the current coordinate data;
- the guidance display contains an indicator array indicating, for each coordinate component, a match and a proximity between the recorded coordinate data and the current coordinate data; and wherein
- the indicator array comprises a plurality of indicators corresponding to a plurality of coordinate components; and
- each of the plurality of indicators includes an indicator element indicating the match, an indicator element indicating the proximity in one direction, and an indicator element indicating the proximity in the other direction.

8. An ultrasound diagnosis apparatus according to claim 7, further comprising: a display device which displays a current ultrasound image, a past ultrasound image, and the probe operation support information.

9. An ultrasound diagnosis apparatus according to claim 7, wherein the probe operation support information contains a reference image, the reference image contains a first graphical object generated based on the recorded coordinate data and a second graphical object generated based on the current coordinate data, and the second graphical object moves corresponding to a movement of the probe.

10. The ultrasonic diagnostic apparatus according to claim 1, wherein the coordinate measuring unit comprises a magnetic sensor provided on said ultrasonic probe and a magnet field generator is provided at a fixed location whereby a three-dimensional position and orientation of said ultrasonic probe is measured.

* * * * *